US009103777B2

(12) United States Patent
Ralston et al.

(10) Patent No.: US 9,103,777 B2
(45) Date of Patent: *Aug. 11, 2015

(54) MODULAR ANALYTE MEASUREMENT SYSTEM WITH EXTENDABLE STRIP PORT

(71) Applicant: Abbott Diabetes Care Inc., Alameda, CA (US)

(72) Inventors: Hila Ralston, San Leandro, CA (US); Frederic Arbogast, San Ramon, CA (US); Matthew Simmons, Pleasanton, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/248,855

(22) Filed: Apr. 9, 2014

(65) Prior Publication Data

US 2014/0216951 A1     Aug. 7, 2014

Related U.S. Application Data

(63) Continuation of application No. 13/297,091, filed on Nov. 15, 2011, now Pat. No. 8,702,928.

(60) Provisional application No. 61/416,239, filed on Nov. 22, 2010.

(51) Int. Cl.
| | |
|---|---|
| *G01N 27/327* | (2006.01) |
| *G01N 27/416* | (2006.01) |
| *A61B 5/145* | (2006.01) |
| *A61B 5/15* | (2006.01) |
| *G06F 19/00* | (2011.01) |
| *A61B 5/00* | (2006.01) |
| *G01N 33/487* | (2006.01) |

(52) U.S. Cl.
CPC .............. *G01N 27/416* (2013.01); *A61B 5/002* (2013.01); *A61B 5/14532* (2013.01); *A61B 5/150358* (2013.01); *G01N 33/48792* (2013.01); *G06F 19/3468* (2013.01); *A61B 2560/045* (2013.01); *A61B 2560/0443* (2013.01)

(58) Field of Classification Search
CPC .............. G01N 27/3273; G06F 19/322; G06F 19/3418; A61B 5/0022
See application file for complete search history.

(56) References Cited

U.S. PATENT DOCUMENTS

| | | |
|---|---|---|
| 4,545,382 A | 10/1985 | Higgins et al. |
| 4,711,245 A | 12/1987 | Higgins et al. |
| 5,262,035 A | 11/1993 | Gregg et al. |
| 5,262,305 A | 11/1993 | Heller et al. |

(Continued)

*Primary Examiner* — Jennifer Dieterle
(74) *Attorney, Agent, or Firm* — Edward J. Baba; Bozicevic, Field & Francis LLP

(57) ABSTRACT

A modular analyte measurement system having a removable strip port module. In one embodiment, the analyte measurement system includes: an analyte meter; a removable strip port module; and a connector linking the removable strip port module to the analyte meter. The analyte meter includes: a meter housing; a receptacle formed in the meter housing; a processing circuit disposed within the housing; and an input interface within the receptacle and electrically coupled to the processing circuit. The removable strip port module includes: a module housing sized to at least partially fit within the receptacle of the analyte meter; an analyte test strip port disposed within the module housing to receive an analyte test strip via an aperture formed in the module housing; and an output interface coupled to the analyte test strip port. The connector links the output interface with the input interface.

16 Claims, 11 Drawing Sheets

(56) References Cited

U.S. PATENT DOCUMENTS

| | | |
|---|---|---|
| 5,264,104 A | 11/1993 | Gregg et al. |
| 5,320,725 A | 6/1994 | Gregg et al. |
| 5,356,786 A | 10/1994 | Heller et al. |
| 5,509,410 A | 4/1996 | Hill et al. |
| 5,536,249 A | 7/1996 | Castellano et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 5,925,021 A | 7/1999 | Castellano et al. |
| 6,071,391 A | 6/2000 | Gotoh et al. |
| 6,120,676 A | 9/2000 | Heller et al. |
| 6,121,009 A | 9/2000 | Heller et al. |
| 6,143,164 A | 11/2000 | Heller et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,281,006 B1 | 8/2001 | Heller et al. |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,616,819 B1 | 9/2003 | Liamos et al. |
| 6,618,934 B1 | 9/2003 | Feldman et al. |
| 6,638,716 B2 | 10/2003 | Heller et al. |
| 6,676,816 B2 | 1/2004 | Mao et al. |
| 6,730,200 B1 | 5/2004 | Stewart et al. |
| 6,733,328 B2 | 5/2004 | Lin et al. |
| 6,736,957 B1 | 5/2004 | Forrow et al. |
| 6,746,582 B2 | 6/2004 | Heller et al. |
| 6,749,740 B2 | 6/2004 | Funderburk et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,942,518 B2 | 9/2005 | Liamos et al. |
| 7,041,468 B2 | 5/2006 | Drucker et al. |
| 7,077,328 B2 | 7/2006 | Krishnaswamy et al. |
| 7,167,818 B2 | 1/2007 | Brown |
| 7,299,082 B2 | 11/2007 | Feldman et al. |
| 7,488,216 B2 * | 2/2009 | Cho ............................... 439/638 |
| 7,896,703 B2 * | 3/2011 | Stafford et al. ................ 439/638 |
| 7,896,704 B2 * | 3/2011 | Stafford et al. ................ 439/638 |
| 2004/0186365 A1 | 9/2004 | Jin et al. |
| 2004/0254434 A1 | 12/2004 | Goodnow et al. |
| 2006/0025662 A1 | 2/2006 | Buse et al. |
| 2006/0091006 A1 | 5/2006 | Wang et al. |
| 2006/0224141 A1 | 10/2006 | Rush et al. |
| 2007/0068807 A1 | 3/2007 | Feldman et al. |
| 2007/0095661 A1 | 5/2007 | Wang et al. |
| 2007/0108048 A1 | 5/2007 | Wang et al. |
| 2007/0149897 A1 | 6/2007 | Ghesquiere et al. |
| 2007/0199818 A1 | 8/2007 | Petyt et al. |
| 2008/0066305 A1 | 3/2008 | Wang et al. |
| 2008/0102441 A1 | 5/2008 | Chen et al. |
| 2008/0119709 A1 | 5/2008 | Wang et al. |
| 2008/0148873 A1 | 6/2008 | Wang |
| 2008/0167578 A1 | 7/2008 | Bryer et al. |
| 2008/0234559 A1 | 9/2008 | Arbogast et al. |
| 2008/0267823 A1 | 10/2008 | Wang et al. |
| 2009/0095625 A1 | 4/2009 | Forrow |
| 2009/0255811 A1 | 10/2009 | Forrow et al. |
| 2009/0270696 A1 | 10/2009 | Arbogast et al. |
| 2010/0015860 A1 | 1/2010 | Stafford et al. |
| 2010/0064800 A1 | 3/2010 | Stafford et al. |
| 2010/0065426 A1 | 3/2010 | Stafford et al. |
| 2010/0198034 A1 | 8/2010 | Thomas et al. |
| 2010/0198142 A1 | 8/2010 | Sloan et al. |
| 2010/0213057 A1 | 8/2010 | Feldman et al. |
| 2010/0325868 A1 | 12/2010 | Wang et al. |
| 2010/0326842 A1 | 12/2010 | Mazza et al. |
| 2011/0040246 A1 | 2/2011 | Galasso |
| 2011/0184264 A1 | 7/2011 | Galasso et al. |
| 2012/0100601 A1 * | 4/2012 | Simmons et al. .......... 435/287.7 |

\* cited by examiner

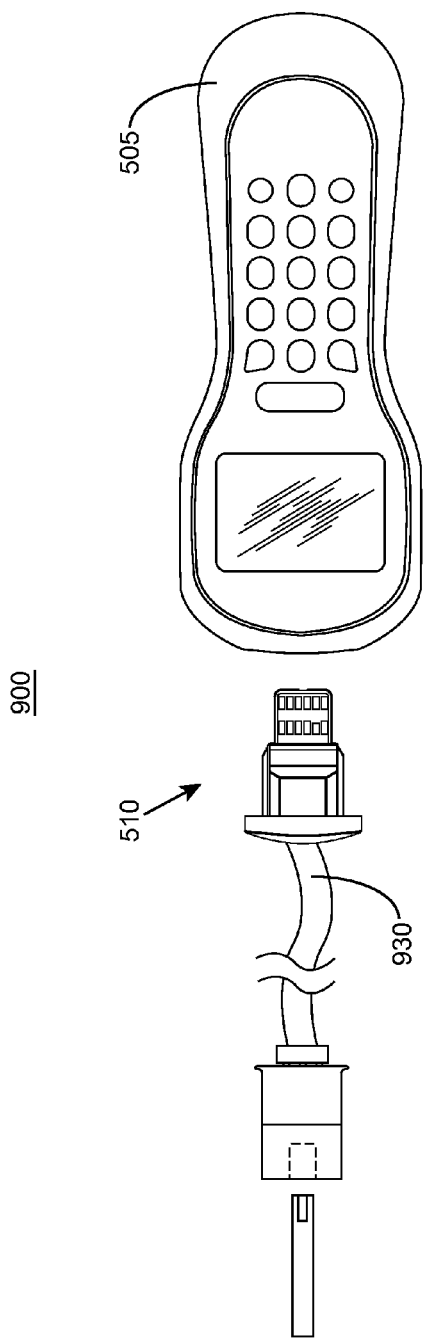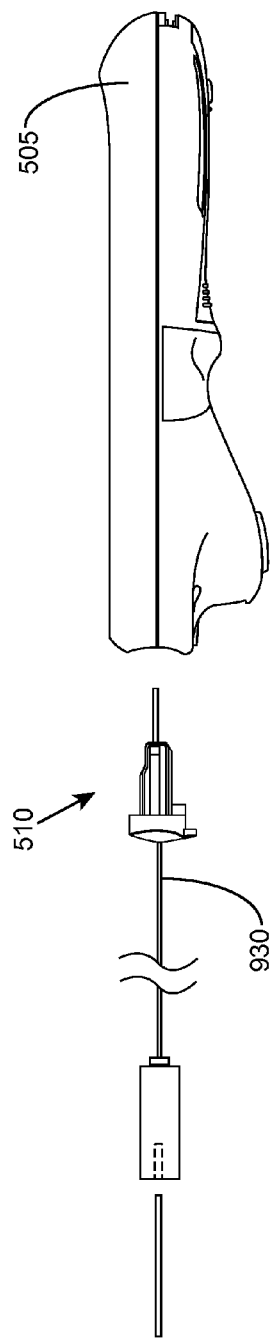
FIG. 9
FIG. 10

MODULAR ANALYTE MEASUREMENT SYSTEM WITH EXTENDABLE STRIP PORT

CROSS-REFERENCE TO RELATED APPLICATIONS

This application is a continuation of application Ser. No. 13/297,091, filed on Nov. 15, 2011, now U.S. Pat. No. 8,702,928, which claims the benefit of U.S. Provisional Application No. 61/416,239, filed on Nov. 22, 2010, which is herein incorporated by reference in its entirety.

RELEVANT APPLICATIONS

This application is related to U.S. patent application Ser. No. 12/175,279, filed on Jul. 17, 2008. This application is also related to U.S. patent application Ser. No. 12/495,662, filed on Jun. 30, 2009, and Ser. No. 12/624,231, filed on Nov. 23, 2009, both of which claim priority to U.S. patent application Ser. No. 12/175,279. This application is also related to U.S. Provisional Patent Application No. 61/406,860, filed Oct. 26, 2010. The disclosures of the above-mentioned applications are incorporated herein by reference in their entirety.

BACKGROUND OF THE INVENTION

1. The Field of the Invention

The present invention relates to analyte measurement systems. More specifically, the present invention relates to analyte measurement systems having a removable strip port module.

2. Background

One of the tools used in diabetes management is an analyte measurement device (or analyte meter). An analyte measurement device is typically used to measure the blood glucose level of a person based on a sample of blood. In practice, a user inserts an analyte test strip into a test strip port of the measurement device. The user then lances her finger to obtain a small sample of blood. The blood sample is then placed onto the analyte test strip, and the measurement device analyzes the blood sample. The measurement device then typically displays a blood glucose level from the analysis.

In order to ensure an accurate measurement is being generated, it is necessary to keep the measurement device free from contamination. There are instances where the strip port may become contaminated with blood or other fluids (e.g., calibration fluid). When this occurs, the performance of the measurement device suffers and the user is no longer assured an accurate result. As such, the user may need to purchase a new measurement device.

Dedicated hospital meters, for example, have high occurrence rates of contamination due to factors such as heavy use, need for calibration, disinfection protocols, and other environmental factors. Contamination of a hospital meter, and the subsequent need to replace the hospital meter, is costly. Further, the inventors have found that a substantial number of hospital meters are returned to the manufacturer simply because the strip port has been contaminated, while most of the other parts of the meter remain entirely functional.

Additionally, hospital meters that are used in isolation facilities are subject to strict disinfection protocols to ensure that the meter is free from bacteria or harmful microorganisms. Such protocols include harsh cleaning agents, as well as specialized carrying cases or isolation bags to prevent the meter from contacting a patient.

Another disadvantage of typical hospital meters is that they are many times too large and cumbersome for neonatal screening. Typical hospital meters are difficult to maneuver within the restricted confines of a neonate bed. While portable hand-held blood analyte meters have been available for many years, most portable hand-held meters are intended for self-monitoring of individuals, and lack the functionality of professional dedicated hospital meters. Dedicated hospital meters, for example, include functionality such as (but not limited to): multiple patient use; tracking of patient and/or operated identification; barcode scanning of patient, operator, or test strips; database management; data transfer; system-wide connectivity; etc.

BRIEF SUMMARY

Presented herein is a modular analyte measurement system having a removable strip port module. Embodiments of the present invention relate to modular components of the analyte measurement system. In one embodiment, for example, there is provided an analyte measurement system, comprising: an analyte meter; a removable strip port module; and a connector linking the removable strip port module to the analyte meter. The analyte meter includes: a meter housing; a receptacle formed in the meter housing; a processing circuit disposed within the housing; and an input interface within the receptacle and electrically coupled to the processing circuit. The removable strip port module includes: a module housing sized to at least partially fit within the receptacle of the analyte meter; an analyte test strip port disposed within the module housing to receive an analyte test strip via an aperture formed in the module housing; and an output interface coupled to the analyte test strip port. The connector links the output interface with the input interface.

BRIEF DESCRIPTION OF THE FIGURES

The accompanying drawings, which are incorporated herein, form part of the specification. Together with this written description, the drawings further serve to explain the principles of, and to enable a person skilled in the relevant art(s), to make and use the present invention.

FIG. 9 illustrates a plan view of an analyte measurement system, in accordance with one embodiment presented herein.

FIG. 10 illustrates a side view of the analyte measurement system of FIG. 9.

DETAILED DESCRIPTION OF THE INVENTION

Figure 1:
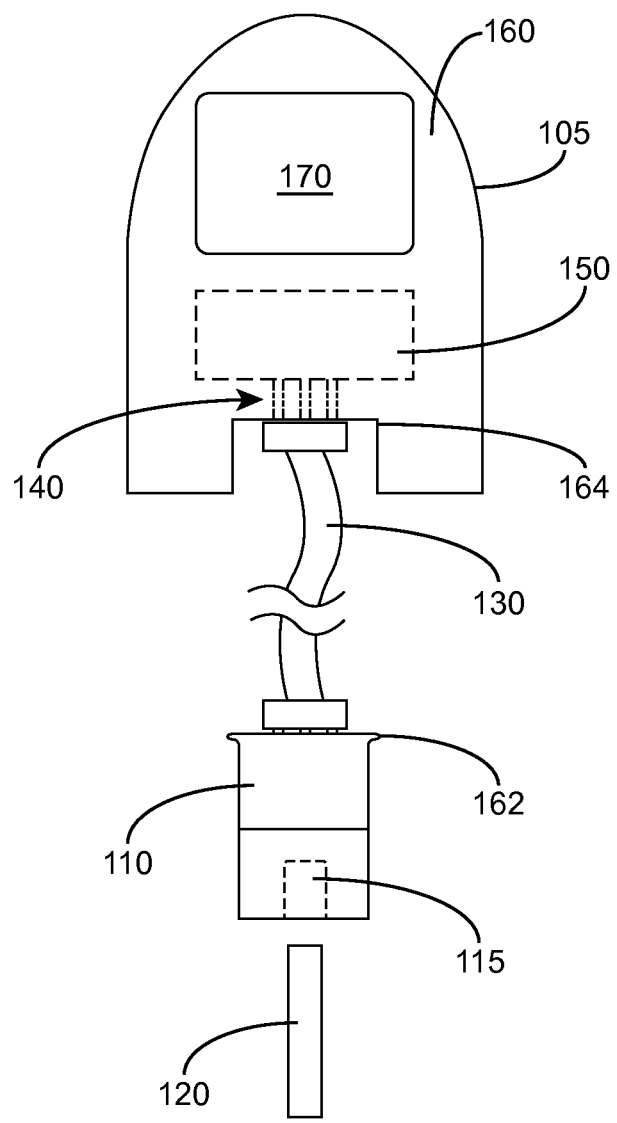
FIG. 1 illustrates a plan view of an analyte measurement system, including an analyte meter and a removable strip port module.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be limited only by the appended claims.

Embodiments presented herein relate to systems and methods where a relatively smaller sub-assembly (e.g., removable strip port module) serves as an extension of a dedicated hospital analyte meter. The sub-assembly is designed to facilitate "bedside" testing of a patient. For example, in one embodiment, a removable strip port module is connected to an analyte meter through a physical connection, such as an extension cable. In another embodiment, the removable strip port module is connected to the analyte meter through a wireless interface. During testing, the removable strip port module can be separated from the meter and used to test the patient. As such, the meter does not need to be carried to the patient.

In one embodiment, a removable strip port module is a mechanical and electrical sub-assembly that "plugs" into the Analog Front End (AFE) of an analyte meter via a connector. The connector may be a cable, cord, or other extension piece that routes data and/or other electrical signals from the removable strip port module to the meter. The removable strip port module and/or meter may include mechanical engagement features to house the module and/or assist in the connection between the module and the meter.

In one embodiment, the removable strip port module includes a test strip receptacle mounted on a printed circuit board assembly (PCBA) daughter-card. The test strip receptacle and PCBA daughter-card are then enclosed in a module housing with a slit or aperture at one end, for the strip port opening, and an opening for a cable exiting on the other end. The cable is attached to the PCBA daughter-card, for example, through soldering or heat-bar. The opposite end of the cable may have a connector to interface with a mating connector within the meter. The cable may be a fixed length or retractable/extendable. The PCBA daughter-card may also have active components, such as op-amps, and supporting passive components in order to enhance the signal strength and assure adequate electrical signal levels reach the meter AFE. Alternative embodiments may include a rigid flex cable design; a press-fit engagement between the module and the meter; a through-hole in the meter for cable access; surface mounted connectors; a ribbon cable; mechanical potting; and one-time or multiple use connection option.

The removable strip module may also transfer signals from the strip port connector to the meter through a non-physical connection, such as a wireless connection. In such embodiment, the removable strip port module PCBA would also include a power supply and active components to support a wireless data transfer module. The meter would also include a wireless transceiver to support data transfer. The wireless connection may be a standard type, such as IEEE 802.11, or a proprietary wireless bus protocol. With a wireless removable strip port module, there would be no need for a cable, and the module would thus "detach" from the meter when needed for testing.

Prior to detaching the module from the meter, the meter can be configured to charge a power supply on the removable module (e.g., a rechargeable battery or capacitor). The module may also be directly charged through a separate power supply.

As such, in one embodiment, there is provide an analyte measurement system including a dedicated hospital meter and one or more removable strip port modules in wireless communication with the meter. Each of the removable strip port modules can be kept "bedside" with a patient, and transmit test data back to the meter when appropriate. As such, each removable strip port module can be maintained in a sterile, isolated facility, with each patient, while a single dedicated hospital meter receives and processes that data from each removable strip port module. Further, such system removes the need for the healthcare provider to disinfect the dedicated hospital meter when testing across patients; a practice that many healthcare providers complain about. Further, in such embodiment, each removable strip port module may transmit data under a unique RFID code. The dedicated hospital meter then includes decoding circuitry to identify from where the received data is being transmitted.

In certain embodiments, the removable strip port modules described herein are configured for real-time data/signal transfer to a meter via a connector. In other embodiments, the removable strip port modules described herein include a processor and memory unit for signal-to-data conversion and temporary storage of the analyte data. The removable strip port module may then be "plugged" into the meter for downloading of the analyte data.

The following detailed description of the figures refers to the accompanying drawings that illustrate an exemplary embodiment of an analyte measurement system. Other embodiments are possible. Modifications may be made to the embodiment illustrated without departing from the spirit and scope of the present invention. Therefore, the following detailed description is not meant to be limiting.

FIG. 1 illustrates a plan view of an analyte measurement system 100, including an analyte meter 105 and a removable strip port module 110. As shown, removable strip port module 110 includes a test strip receptacle 115 for receiving an analyte test strip 120. While test strip receptacle 115 is provided on the opposite side of the output interface of module 110, test strip receptacle 115 may be provided on any side of module 110. Removable strip port module 110 also includes an output interface that is electrically coupled to an input interface (e.g., AFE) of analyte meter 110 via a connector 130, such as a cable, cord, serial/parallel bus, or other equivalent connector means. Internal contacts or traces 140 transmit electrical signals and/or data between connector 130 and a processing unit 150 within a meter housing 160 of analyte meter 105.

Further, removable strip port module 110 may be sized and shaped to at least partially fit within a receptacle formed in housing 160 of analyte meter 105. Module 110 may further include one or more retention tabs 162, which are configured to align and/or engage module 110 to receiving tabs 164 on meter housing 160. The interface between module 110 and meter housing 160 may be configured to be substantially impervious to contaminants. In another embodiment, module 110 may be coupled to meter 105 via a press-fit or snap-fit engagement.

Analyte meter 105 may further include a user interface 170, such as a touch-screen monitor to display test results and receive input from a user.

In one embodiment, connector 130 and internal traces 140 may include a variety of data transfer channels. For example, connector 130 and internal traces 140 may include three channels plus a ground channel for one type of removable strip port module, three channels plus a ground channel for a second type of removable strip port module, a channel to identify the removable strip port module, and a channel to identify what type of test strip is being used (e.g., glucose, ketone, etc.). As such, connector 130 and internal traces 140 increase the functionality of analyte meter 105 by allowing it to be used with multiple different removable strip port modules.

Figure 2:
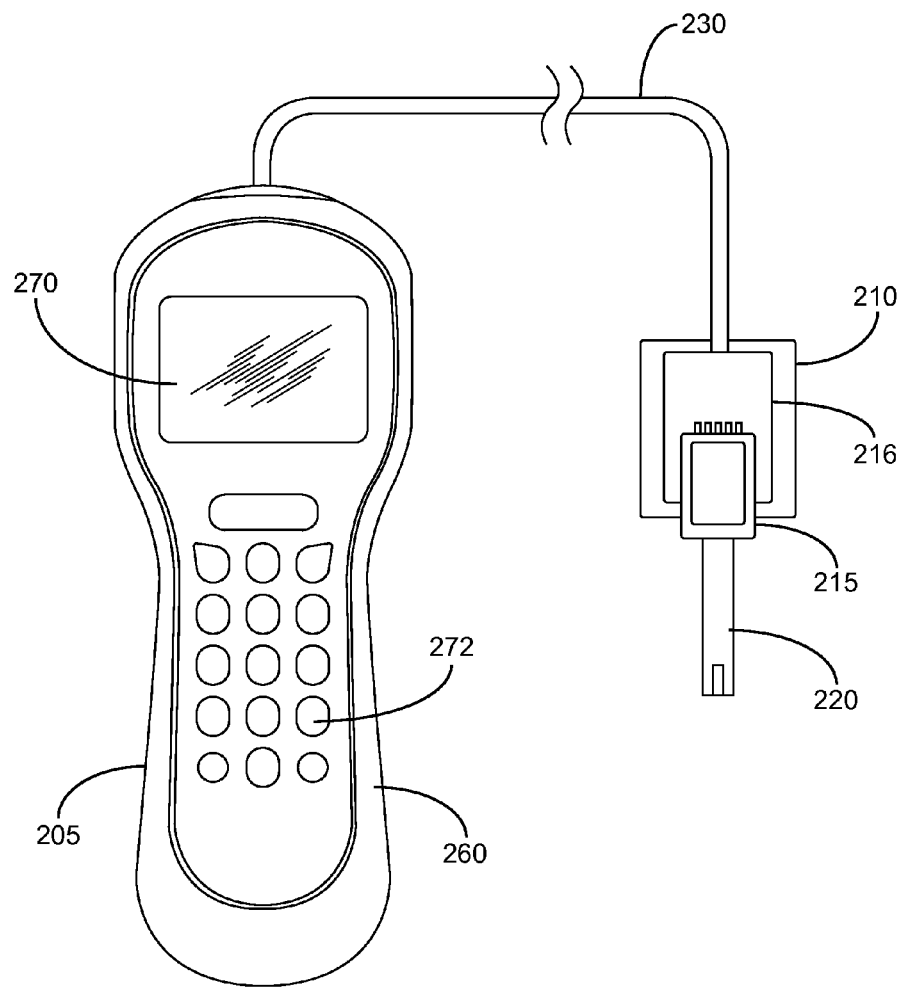
FIG. 2 illustrates a plan view of an analyte measurement system, including an analyte meter and a removable strip port module, in accordance with an alternative embodiment presented herein.

FIG. 2 illustrates a plan view of an analyte measurement system 200, including an analyte meter 205 and removable strip port module 210, in accordance with an alternative embodiment presented herein. As shown, removable strip port module 210 includes a test strip receptacle 215 for receiving an analyte test strip 220. Removable strip port module 210 also includes an output interface that is electrically coupled to an input interface of analyte meter 205 via a connector 230; such as a cable, cord, serial/parallel bus, or other equivalent connector means. Connector 230 may be a fixed length cable, or a retractable cord. Connector 230 may also include a winding mechanism to provide variable length extension. One such winding mechanism is described in U.S. Pat. No. 6,733,328, which is herein incorporated by reference in its entirety.

Test strip receptacle 215 is mounted on a PCBA daughter-card 216, for electrical communication between test strip receptacle 215 and connector 230. As shown, test strip receptacle 215 is provided on the opposite side of the output interface of module 210. However, test strip receptacle 215 may be provided on any side of module 210.

In the embodiment shown, removable strip port module 110 is not configured to fit within a receptacle formed in the meter housing 260. Instead, module 110 is provided as an independent unit that electrically couples to meter 205 only through connector 230.

Analyte meter 205 may include a user interface, such as a display 270 and hard/soft buttons 272.

Figure 3:
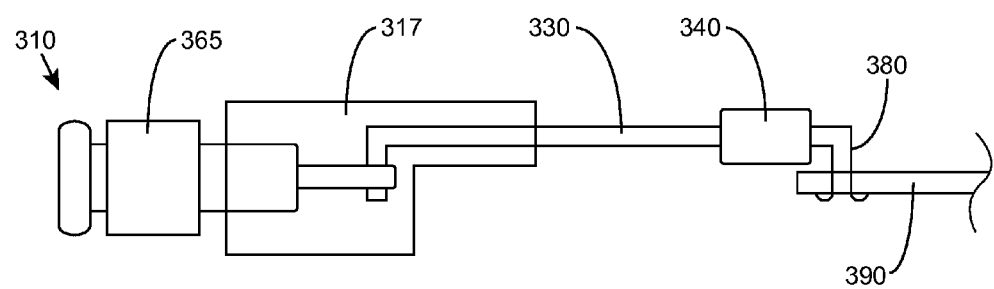
FIG. 3 illustrates a side view of an alternative connector form.
Figure 4:
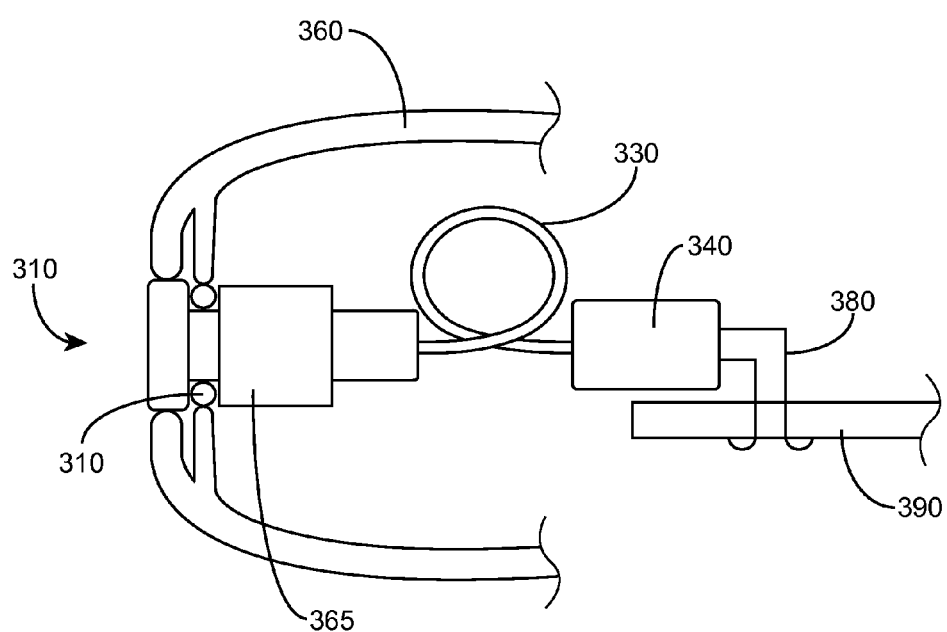
FIG. 4 illustrates the removable strip port module of FIG. 3, provided within a section of an analyte meter.

FIG. 3 illustrates a side view of an alternative connector form between removable strip port module 310 and an input interface 340 in an analyte meter. FIG. 4 illustrates removable strip port module 310 within a section of meter housing 360. In the embodiment shown, removable strip port module 310 is electrically coupled to input interface 340 within an analyte meter via connector 330. In such embodiment, connector 330 is a soldered wire electrically coupled to leads in module 310. A heat sink 317 may be provided for thermal control of connector 330. Electrical current flows from module 310 to interface 340, and then to PCBA 390 via contacts 380.

FIG. 4 illustrates the removable strip port module 310 installed within meter housing 360. A gasket 365 aligns and maintains removable strip port module 310 within meter housing 360. A second gasket 366, such as an o-ring, may also be employed to further align and maintain removable strip port module 310 in place, as well as keep contaminants from entering meter housing 360. As shown in FIG. 4, connector 330 may be looped during installation and tucked within meter housing 360. Connector 330 is provided with additional length to provide flexibility and functionality to the system. In the event that a user wishes to perform an analyte test at a distance from the meter, removable strip port module 310 may be withdrawn from meter housing 360 and an analyte test may be performed while the module 310 and meter remain connected through connector 330.

Figure 5:
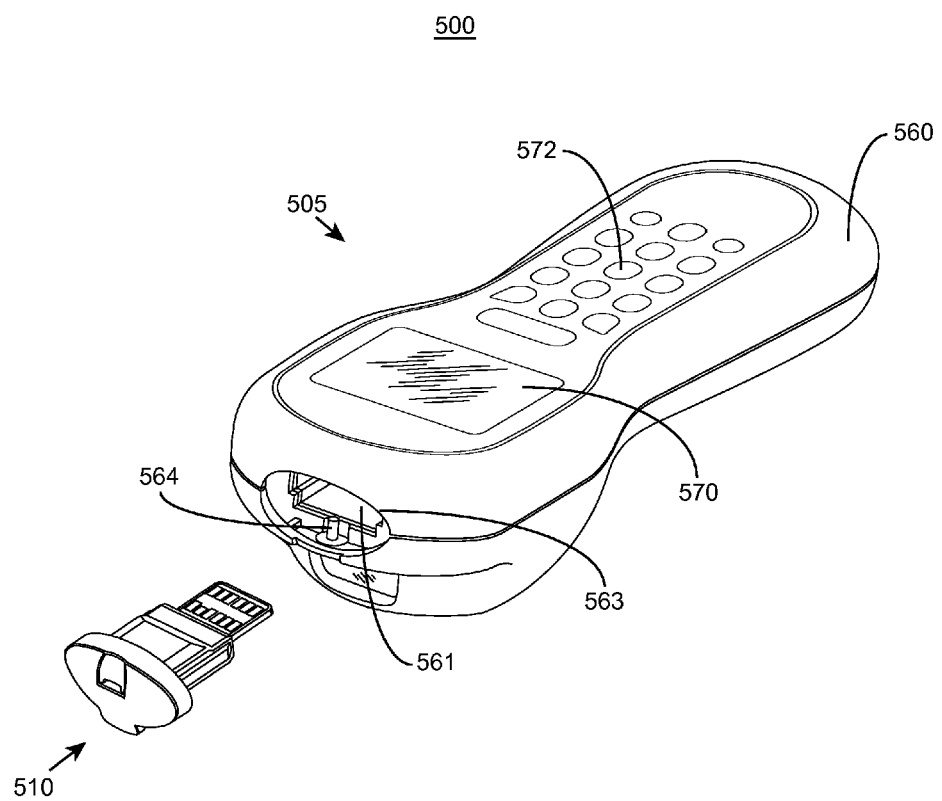
FIG. 5 is a perspective view of an analyte measurement system, in accordance with one embodiment presented herein.

FIG. 5 is a perspective view of an analyte measurement system 500, in accordance with one embodiment presented herein. System 500 includes a removable strip port module 510 and an analyte meter 505. FIG. 5 illustrates system 500 prior to insertion of removable strip port module 510 into analyte meter 505.

Analyte meter 505 may be similar to analyte meters known in the art. For example, analyte meter 505 may include similar structures, functions, and components as the analyte meters described in U.S. Pat. No. 7,077,328, which is incorporated herein by reference in its entirety. As shown, analyte meter 505 includes a display panel 570 for displaying instructions and/or results from an analyte measurement, and a user interface 572 for inputting commands to the analyte meter. Analyte meter 505 also includes internal processing units (not shown) for the analysis of a blood sample. As such, analyte meter 505 includes means for analyzing an electrical signal received from removable strip port module 510. Analyte meter 505, however, has been modified to lack a fully integrated analyte test strip port. Instead, analyte meter 505 includes an input interface (e.g., AFE) with a wireless data transceiver to receive data from removable strip port module 510.

The transmission of data between removable strip port module 510 and the AFE of meter 505 may be a wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

As shown in FIG. 5, analyte meter 505 includes a receptacle 505 that provides an opening in the analyte meter housing 560. Removable strip port module 510 is designed to fit within receptacle 561. Guide features 563 are provided in the meter housing 560 to aide in the insertion and alignment of removable strip port module 510 within receptacle 561. Analyte meter 505 also includes a coupling feature 564 (e.g., a screw hole), which aligns with module 510 for permanent or temporary attachment. Alternative attachment means may also be employed to removably (or semi-permanently) attach removable strip port module 510 to analyte meter 505.

In one embodiment, for example, the meter housing 560 and internal components are formed of medical grade PC/ABS plastic blend, and may include an anti-microbial plastic such as BAYER BAYBLEND AM120FR. In one embodiment, meter housing 560 is formed of two or more separate components, which are screwed together using M3 stainless steel screws. Such screws may have heads that differentiate them from the strip port retaining screws. For example, such screws may have Torx heads. Internal screws may be M2.5 zinc-plated, pan head Philips screws.

Figure 6:
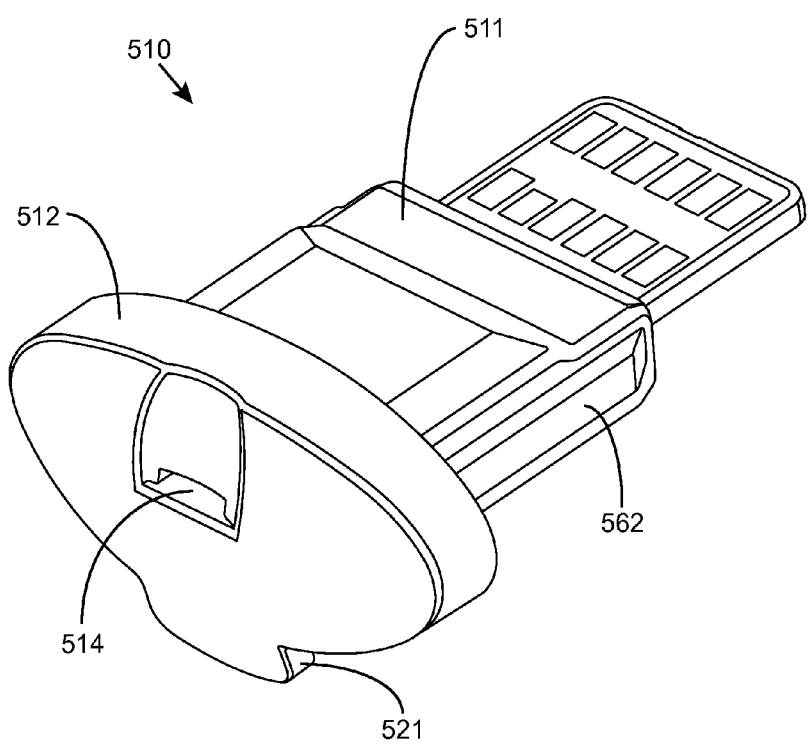
FIG. 6 is a perspective view of a removable strip port module, in accordance with one embodiment presented herein.
Figure 7:
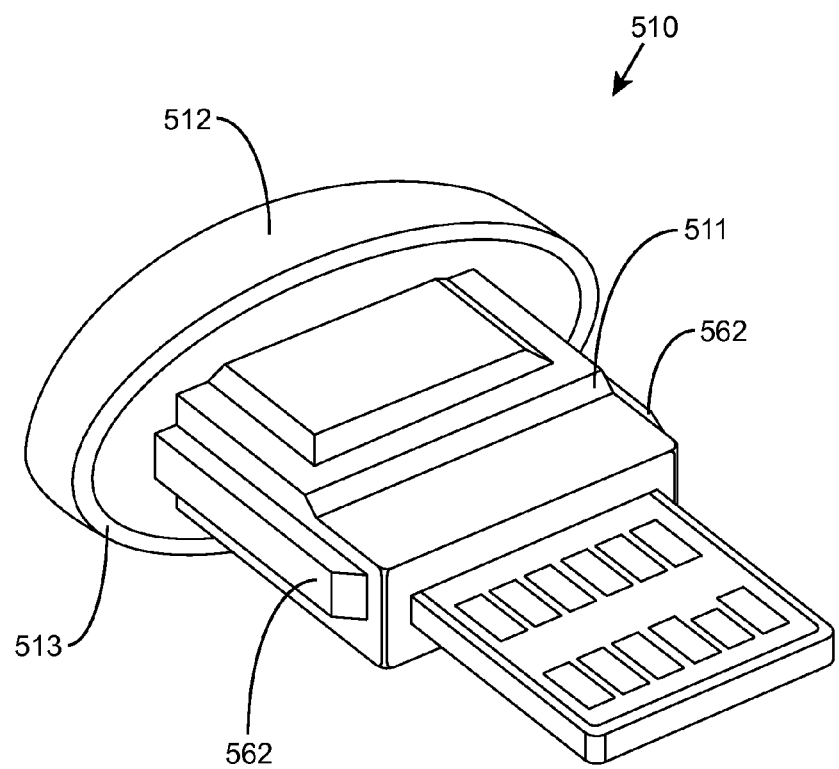
FIG. 7 is a rear perspective view of the removable strip port module of FIG. 6.
Figure 8:
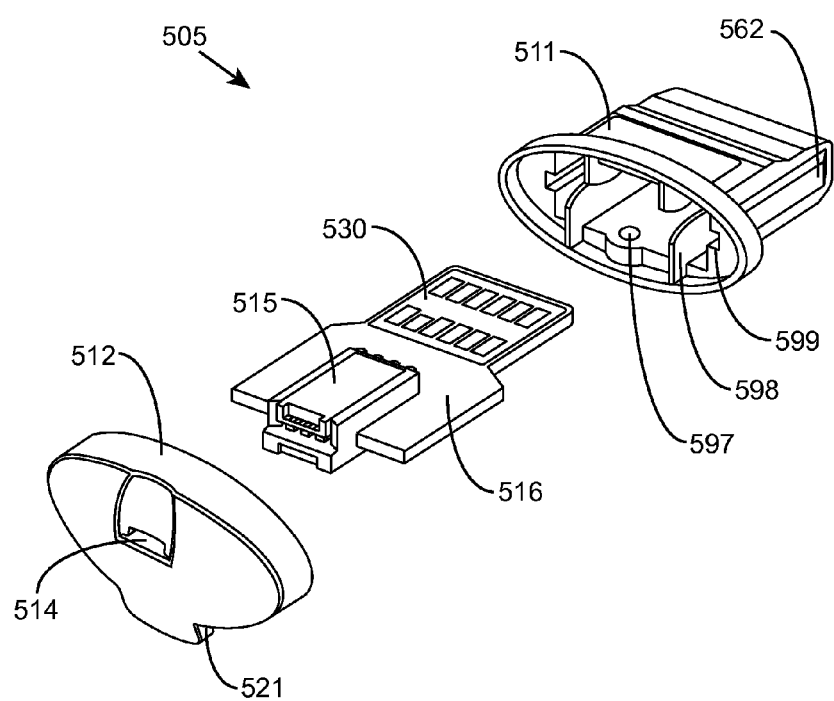
FIG. 8 is an exploded view of a removable strip port module, in accordance with one embodiment presented herein.

FIG. 6 is a perspective view of removable strip port module 510, in accordance with one embodiment presented herein. FIG. 7 is a rear perspective view of removable strip port module 510. FIG. 8 is an exploded view of removable strip port module 510, in accordance with one embodiment presented herein.

As shown in FIGS. 6-8, removable strip port module 510 includes a module housing 511 with a cap 512. An analyte test strip port 515 is disposed within an open end of module housing 511, which is then enclosed (or covered) by cap 512. In one embodiment, analyte test strip port 515 is an electrochemical strip port. In an alternative embodiment, analyte test strip port 515 is an optical strip port. As shown in FIG. 8, analyte test strip port 515 is coupled to a PCBA 516, and electrical leads of analyte test strip port 515 are electrically coupled to a wireless transceiver 530 on PCBA 516. In one embodiment, module 510 may further include a processor (not shown) and/or power source (not shown) mounted on PCBA 516. The power source may be an individual power source, or a rechargeable power source (e.g., a capacitor) that is charged via a connection to meter 505 when module 510 is plugged into the meter.

In one embodiment, module housing 511 is formed of a plastic mold, and more preferably an anti-microbial plastic mold. In alternative embodiments, module housing 511 may be formed of other suitable materials such as plastics, rubbers, polymers, or other inert materials. In one embodiment, for example, module housing 511 and internal components are formed of medical grade PC/ABS plastic blend, and may include an anti-microbial plastic such as BAYER BAYBLEND AM120FR. In the embodiment shown in FIG. 8, module housing 511 includes internal alignment features, such as internal alignment baffles 598 and internal alignment grooves 599, to properly align analyte test strip port 515 and PCBA 516 within module housing 511. Such internal alignment features, and structures equivalent thereto, serve as means for aligning an analyte test strip port within the module housing. A screw hole 597 may be provided in module housing 511 to attach removable strip port module 510 to an analyte meter. A screw for use in screw hole 597 may be a stainless steel, pan head Philips, thread-forming screw.

Module housing 511 also includes external alignment features or guides 562 and beveled surfaces to further support the proper insertion and alignment of removable strip port module 510 within an analyte meter. Such external alignment features, and structures equivalent thereto, serve as means for aligning a removable strip port module within an analyte meter.

Cap 512 serves to fully encase analyte test strip port 515 within module housing 511. In one embodiment, cap 512 is permanently attached to module housing 511 with a hermetic seal 513. In an alternative embodiment, cap 512 may be removably attached to module housing 511. In another alternative embodiment, a gasket means (e.g., a rubber o-ring, fabric, etc.) may be used to seal the gap between cap 512 and module housing 511. In the embodiment shown, cap 512 also includes an optional tab extension 521 to facilitate in the insertion and removal of removable strip port module 510 from an analyte meter.

Cap 512 further includes an aperture 514, which provides access to analyte test strip port 515. In operation, an analyte test strip is inserted through aperture 514 and into analyte test strip port 515. In one embodiment, aperture 514 provides sufficient clearance to accept a wide variety of different analyte test strips form factors. In an alternative embodiment, aperture 514 may be customized to receive a specific analyte test strip form factor. Customizing the aperture size or shape to a specific analyte test strip form factor can prevent the use of non-matching or incompatible analyte test strips with analyte test strip port 515. Aperture 514 may also be formed with a one-way valve or port protector to swipe across the surface of an analyte test strip when the analyte test strip is passed through aperture 514. Such an embodiment may be used to protect analyte test strip port 515 from unwanted contaminants. In alternative embodiments, aperture 514 may incorporate one or more port protectors, such as disclosed in U.S. Patent Application Publication No. 2009/0270696, which is incorporated by reference herein in its entirety.

In the event that unwanted fluids and contaminants enter through aperture 514 and comprise the function of analyte test strip port 515, removable strip port module 510 can be removed and replaced with a new removable strip port module. The replacement of removable strip port module 510 can be done without discarding or replacing any of the functioning components of analyte meter 505. As such, a user/manufacturer can save money by only replacing the components of the system 500 that have actually been comprised. Further, the use of module 510 simplifies disinfecting procedures because a healthcare provider need only clean the module 510, and not the entire meter 505.

FIG. 9 illustrates a plan view of an analyte measurement system 900, in accordance with one embodiment presented herein. FIG. 10 illustrates a side view of the analyte measurement system of FIG. 9. System 900 is similar to system 500, except that the wireless capability of the removable strip port module 510 are removed. In system 900, the link between the output interface of module 510 and the input interface of meter 505 is provided by a physical wire or cable connection 930. Connection 930 may be modified and customized to be as long as necessary for the applicable use. As such, module 510 may be separated from meter 505, and used for bedside testing and/or incubator setting; e.g., in a neonatal application. As used herein, the term "separated" needs to require a complete disconnection. For example, the module may be separated from the meter, while still electrically coupled/linked via a connector. In essence, the module is "separated" from the meter such that the module may be drawn to the patient without the need of bringing the meter to the patient.

Figure 11:
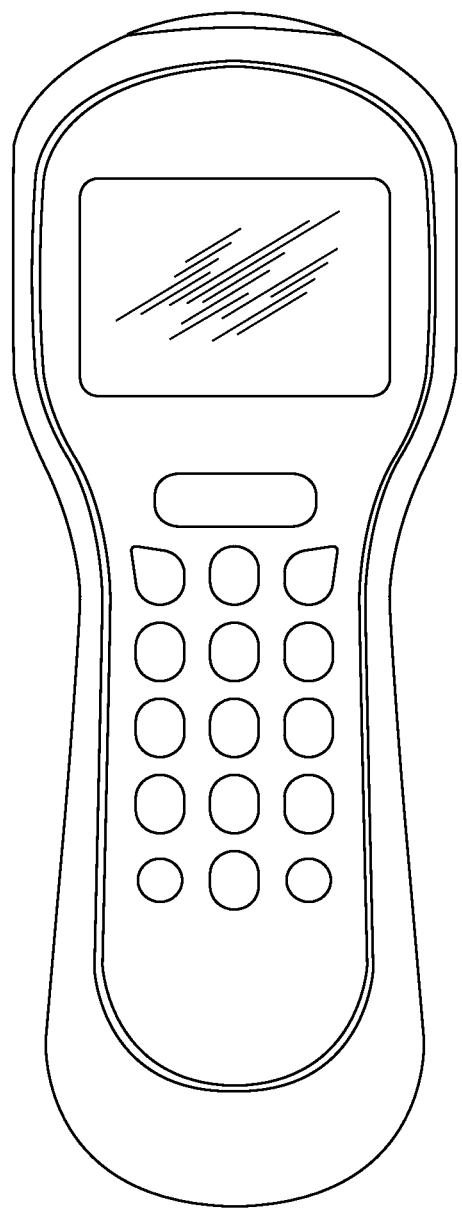
FIG. 11 illustrates a plan view of an analyte measurement system, in accordance with one embodiment presented herein.

FIG. 11 illustrates an ornamental plan view of an analyte measurement system having a removable strip port module at least partially inserted within a receptacle of the meter housing.

Figure 12:
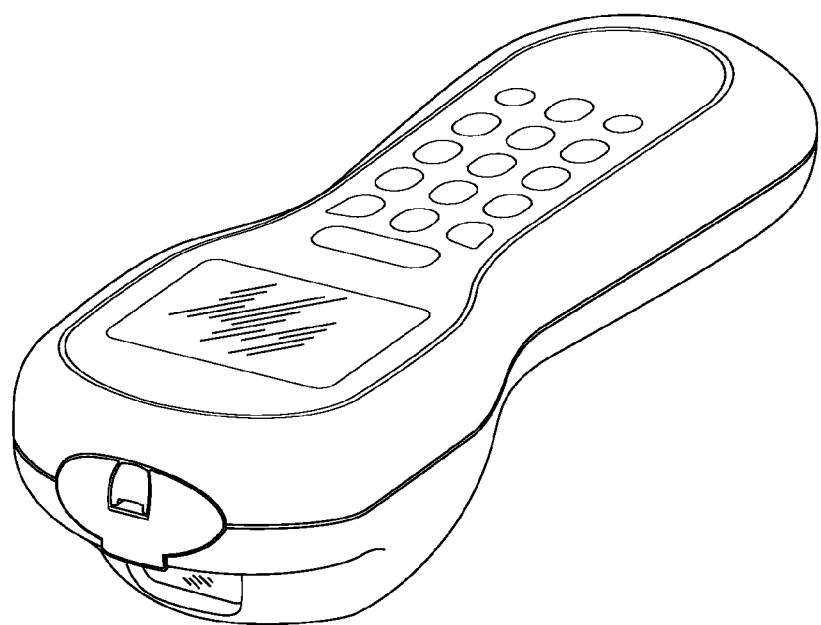
FIG. 12 illustrates a perspective view of the analyte measurement system of FIG. 11.

FIG. 12 illustrates an ornamental perspective view of an analyte measurement system having a removable strip port module at least partially inserted within a receptacle of the meter housing.

Certain embodiments presented herein relate to electrical interfaces in measurement systems. Measurement systems often have electrical interfaces that allow them to electrically connect with another system or apparatus and perform an analysis of an analyte. A system that measures blood glucose levels, for example, includes electrical interfaces that allow the system to measure the blood glucose level from a small blood sample.

Embodiments presented herein also relate to systems and methods that can improve the mean time before failure (MTBF) in measurement systems. By improving the MTBF, a user is provided with a system that lasts longer and has more accurate performance over time.

Embodiments presented herein also relate to strip connectors or strip ports that can be cleaned and/or replaced. The ability to clean or replace a strip port can prevent the system from experiencing problems often associated with port contamination. Blood and other contaminants, for example, can often contaminate a port and make the system unusable or result in inaccurate analysis. A port that can be cleaned or replaced without affecting the operation of the system thus increases the MTBF.

Embodiments presented herein provide further advantages such as: the ability to upgrade strip port modules as new test strip technologies evolve; the ability to clean or sterilize a strip port module; and the ability to allow users to replace strip port modules without returning the entire measurement system to the manufacture.

Certain embodiments relate to in vivo (e.g., continuous monitoring) systems. A continuous monitoring system typically includes a sensor that is worn or placed below the skin, a transmitter that collects glucose information from the sensor, and a receiver that collects the information from the transmitter. The sensor can collect glucose level information continuously, periodically, or at other intervals. Advantageously, a user is relieved from having to repeatedly lance his or her body to collect a blood sample once the sensor is inserted, although the sensor (e.g., an electrochemical sensor that is inserted into a body) can be replaced. U.S. Pat. No. 6,175,752, which is hereby incorporated by reference in its entirety, discloses additional examples of a continuous monitoring system.

Embodiments of the invention further extend to kits. Examples of a kit include a measurement system with one or more removable strip port modules. In some kits, different removable strip port modules are provided for different types of strips. This allows the measurement system to be used with different strip form factors. The kits may also include a plurality of test strips. In certain examples, the measurement system may be configured for use with disposable test strips as well as with test strips that are configured for continuous monitoring systems. Thus, the measurement system may include a receiver to receive information from a transmitter that collects glucose information from an inserted sensor.

Analyte Test Strips

Analyte test strips for use with the present systems can be of any kind, size, or shape known to those skilled in the art; for example, FREESTYLE® and FREESTYLE LITE™ test strips, as well as PRECISION™ test strips sold by ABBOTT DIABETES CARE Inc. In addition to the embodiments specifically disclosed herein, the systems of the present disclosure can be configured to work with a wide variety of analyte test strips, e.g., those disclosed in U.S. patent application Ser. No. 11/461,725, filed Aug. 1, 2006; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; U.S. patent application Ser. No. 12/102,374, filed Apr. 14, 2008, and U.S. Patent Application Publication No. 2009/0095625; U.S. Pat. No. 6,616,819; U.S. Pat. No. 6,143,164; U.S. Pat. No. 6,592,745; U.S. Pat. No. 6,071,391 and U.S. Pat. No. 6,893,545; the disclosures of each of which are incorporated by reference herein in their entirety.

Integrated with Lancing Device

In another embodiment, an analyte measurement system may include an integrated analyte test meter and lancing device for providing a bodily fluid sample, such as a blood sample, and measuring an analyte concentration, such as a blood glucose concentration. Examples of such integrated systems include systems and devices described in US Published Application Nos. US2007/0149897 and US2008/0167578, the disclosures of each of which are incorporated herein by reference in their entirety.

Calculation of Medication Dosage

In one embodiment, the analyte measurement system may be configured to measure the blood glucose concentration of a patient and include instructions for a long-acting insulin dosage calculation function. Periodic injection or administration of long-acting insulin may be used to maintain a baseline blood glucose concentration in a patient with Type-1 or Type-2 diabetes. In one aspect, the long-acting medication dosage calculation function may include an algorithm or routine based on the current blood glucose concentration of a diabetic patient, to compare the current measured blood glucose concentration value to a predetermined threshold or an individually tailored threshold as determined by a doctor or other treating professional to determine the appropriate dosage level for maintaining the baseline glucose level. In one embodiment, the long-acting insulin dosage calculation function may be based upon LANTUS® insulin, available from Sanofi-Aventis, also known as insulin glargine. LANTUS® is a long-acting insulin that has up to a 24 hour duration of action. Further information on LANTUS® insulin is available at the website located by placing "www" immediately in front of ".lantus.com". Other types of long-acting insulin include Levemir® insulin available from NovoNordisk (further information is available at the website located by placing "www" immediately in front of ".levemir-us.com". Examples of such embodiments are described in US Published Patent Application No. US2010/01981142, the disclosure of which is incorporated herein by reference in its entirety.

Docking Station

In another embodiment, the analyte measurement system may include a corresponding docking station or one or more other peripheral devices. The docking station may include, among others, a transmitter whereby when the analyte measurement system is docked to the docking station, the analyte measurement system and docking station may communicate over a data network with, for example, a healthcare provider, for the transfer of data or receipt of instructions or new dosage regimens. The docking station transmitter may be configured for transmission protocols including, but not limited to, cellular telephone transmission, such as code division multiple access (CDMA) or Global System for Mobile communications (GSM), internet communication, facsimile communications, and/or telephone communication. In another aspect, the docking station may also be configured to provide power for recharging a rechargeable battery of the analyte measurement system. In another aspect, the docking station may be configured for communication with a personal computer for additional storage, programming, and/or communication.

In another embodiment, a docking station such as described in U.S. Pat. No. 7,077,328 may be employed. As stated above, U.S. Pat. No. 7,077,328 is incorporated herein by reference in its entirety.

Strip Port Configured to Receive Test Strips for Different Analytes

In another embodiment, there is provided an analyte measurement system for multichemistry testing. The test strips are for chemical analysis of a sample, and are adapted for use in combination with a measuring device having a test port and capable of performing a multiplicity of testing functionalities. Each type of test strip corresponds to at least one of the testing functionalities, and at least some types of test strips have indicators of the testing functionality on them. The test port is adapted for use in combination with a multiplicity of different types of test strips and includes a sensor capable of specifically interacting with the indicator(s) on the test strips, thereby selecting at least one of the multiplicity of testing functionalities corresponding to the type of test strip. Such system would include a strip port that can be used to read a test strip for glucose and a test strip for ketone bodies. Examples of such embodiment are provided in U.S. Pat. No. 6,773,671, which is incorporated herein by reference in it entirety.

Strip Port Configured to Receive Test Strips Having Different Dimensions and/or Electrode Configurations In some embodiments, an analyte measurement system as described herein includes a strip port configured to receive test strips having different dimensions and/or electrode configurations, e.g., as described in the U.S. patent application Ser. No. 12/695,947 filed on Jan. 28, 2010, and entitled "Universal Test Strip Port", the disclosure of which is incorporated by reference herein in its entirety.

Test Strip Ejector

In some embodiments, an analyte measurement system as described herein is configured to include an optional analyte test strip ejector configured to eject an analyte test strip from a test strip port of the analyte measurement system. An analyte test strip ejector may be useful, for example, where it is desirable to eject an analyte test strip containing a sample of bodily fluid, e.g., blood, following an analyte measurement conducted using the analyte measurement system. This allows a user of the analyte measurement system to dispose of the contaminated analyte test strip without touching the analyte test strip.

In some embodiments, the analyte test strip ejector slidably engages a portion of the housing of the analyte measurement system. The analyte test strip ejector may be configured such that upon insertion of an analyte test strip into the test strip port, the analyte test strip ejector is moved rearward with respect to the test strip port and in the direction of insertion. In order to eject the analyte test strip, a user physically moves the analyte test strip ejector forward with respect to the test strip port and in the opposite of the direction of insertion. This movement in-turn exerts force upon the analyte test strip expelling it from the test strip port. Alternatively, the analyte test strip ejector may be configured such that insertion of the analyte test strip into a strip port of the analyte measurement system positions the analyte test strip ejector in a "cocked" position, e.g., by engaging a spring mechanism. The analyte measurement system may include a button, switch, or other suitable mechanism for releasing the cocked ejector from the cocked position such that it ejects the analyte test strip from the strip port of the analyte measurement system. Additional information regarding analyte test strip ejectors is provided in the U.S. patent application Ser. No. 12/695,947, filed on Jan. 28, 2010, and entitled "Universal Test Strip Port."

Splash-Proof Test Strip Port

In some embodiments, an analyte measurement system as described herein is configured to include a contamination resistant test strip port and/or a splash-proof test strip port. In one such embodiment, the test strip port includes one or more sealing members positioned so as to limit and/or prevent internal contamination of the test strip port with fluids and/or particles present in the environment outside the test strip port. In another embodiment, the test strip port includes an internal beveled face which can limit and/or prevent ingress of one or more external contaminants into the internal area of the test strip port.

Additional disclosure and examples of contamination resistant test strip ports are provided in U.S. patent application Ser. No. 12/539,217, filed Aug. 11, 2009, and entitled "Analyte Sensor Ports," the disclosure of which is incorporated by reference herein in its entirety.

In some embodiments, the test strip ports described herein can be configured to work with (e.g., engage with or operate in connection with) additional mechanisms and/or devices designed to limit and/or prevent contamination of the internal areas of the test strip ports themselves or the internal areas of the analyte measurement system into which the test strip ports can be integrated. For example, mechanisms, devices and methods of protecting test strip port openings are described in U.S. Patent Application Publication No. US2008/0234559, and U.S. Patent Application Publication No. US2008/0119709, the disclosure of each of which is incorporated by reference herein in their entirety. Test strip ports according to the present disclosure can also be configured to be replaceable and/or disposable, and/or configured so as to limit and/or prevent contamination of the analyte measurement system in which the test strip port is integrated. Additional description is provided, for example, in U.S. Application Publication No. 2010/0064800, the disclosure of which is incorporated by reference herein it its entirety.

Implanted Analyte Sensor

In some embodiments, an analyte measurement system as described herein may include an implanted or partially implanted analyte sensor, e.g., a system including an implanted or partially implanted glucose sensor (e.g., a continuous glucose sensor). A system including an implanted or partially implanted glucose sensor may include an analyte measurement system as described herein, which is configured to receive analyte data from the implanted or partially implanted glucose sensor either directly or through an intermediate device, e.g., an RF-powered measurement circuit coupled to an implanted or partially implanted analyte sensor. In some embodiments, where an analyte measurement system according to the present disclosure is integrated with an implanted sensor, the analyte measurement system does not include a strip port for receiving an analyte test strip. In one embodiment, the analyte measurement system may be used to calibrate the analyte monitoring system, e.g., using one point calibration or other calibration protocol. For additional information, see U.S. Pat. No. 6,175,752, the disclosure of which is incorporated by reference herein in its entirety. In some embodiments, the analyte measurement system may be configured to communicate with the implanted or partially implanted analyte sensor via Radio Frequency Identification (RFID) and provide for intermittent or periodic interrogation of the implanted analyte sensor.

Exemplary analyte monitoring systems that may be utilized in connection with the disclosed analyte measurement system include those described in U.S. Pat. No. 7,041,468; U.S. Pat. No. 5,356,786; U.S. Pat. No. 6,175,752; U.S. Pat. No. 6,560,471; U.S. Pat. No. 5,262,035; U.S. Pat. No. 6,881,551; U.S. Pat. No. 6,121,009; U.S. Pat. No. 7,167,818; U.S. Pat. No. 6,270,455; U.S. Pat. No. 6,161,095; U.S. Pat. No. 5,918,603; U.S. Pat. No. 6,144,837; U.S. Pat. No. 5,601,435; U.S. Pat. No. 5,822,715; U.S. Pat. No. 5,899,855; U.S. Pat. No. 6,071,391; U.S. Pat. No. 6,120,676; U.S. Pat. No. 6,143,164; U.S. Pat. No. 6,299,757; U.S. Pat. No. 6,338,790; U.S. Pat. No. 6,377,894; U.S. Pat. No. 6,600,997; U.S. Pat. No. 6,773,671; U.S. Pat. No. 6,514,460; U.S. Pat. No. 6,592,745; U.S. Pat. No. 5,628,890; U.S. Pat. No. 5,820,551; U.S. Pat. No. 6,736,957; U.S. Pat. No. 4,545,382; U.S. Pat. No. 4,711,245; U.S. Pat. No. 5,509,410; U.S. Pat. No. 6,540,891; U.S. Pat. No. 6,730,200; U.S. Pat. No. 6,764,581; U.S. Pat. No. 6,299,757; U.S. Pat. No. 6,461,496; U.S. Pat. No. 6,503,381; U.S. Pat. No. 6,591,125; U.S. Pat. No. 6,616,819; U.S. Pat. No. 6,618,934; U.S. Pat. No. 6,676,816; U.S. Pat. No. 6,749,740; U.S. Pat. No. 6,893,545; U.S. Pat. No. 6,942,518; U.S. Pat. No. 6,514,718; U.S. Pat. No. 5,264,014; U.S. Pat. No. 5,262,305; U.S. Pat. No. 5,320,715; U.S. Pat. No. 5,593,852; U.S. Pat. No. 6,746,582; U.S. Pat. No. 6,284,478; U.S. Pat. No. 7,299,082; U.S. Patent Application No. 61/149,639, entitled "Compact On-Body Physiological Monitoring Device and Methods Thereof", U.S. patent application Ser. No. 11/461,725, filed Aug. 1, 2006, entitled "Analyte Sensors and Methods"; U.S. patent application Ser. No. 12/495,709, filed Jun. 30, 2009, entitled "Extruded Electrode Structures and Methods of Using Same"; U.S. Patent Application Publication No. US2004/0186365; U.S. Patent Application Publication No. 2007/0095661; U.S. Patent Application Publication No. 2006/0091006; U.S. Patent Application Publication No. 2006/0025662; U.S. Patent Application Publication No. 2008/0267823; U.S. Patent Application Publication No. 2007/0108048; U.S. Patent Application Publication No. 2008/0102441; U.S. Patent Application Publication No. 2008/0066305; U.S. Patent Application Publication No. 2007/0199818; U.S. Patent Application Publication No. 2008/0148873; U.S. Patent Application Publication No. 2007/0068807; US patent Application Publication No. 2010/0198034; and U.S. provisional application No. 61/149,639 titled "Compact On-Body Physiological Monitoring Device and Methods Thereof", the disclosures of each of which are incorporated herein by reference in their entirety.

Integration with Medication Delivery Devices and/or Systems

In some embodiments, the analyte measurement systems disclosed herein may be included in and/or integrated with, a medication delivery device and/or system, e.g., an insulin pump module, such as an insulin pump or controller module thereof. In some embodiments the analyte measurement system is physically integrated into a medication delivery device. In other embodiments, an analyte measurement system as described herein may be configured to communicate with a medication delivery device or another component of a medication delivery system. Additional information regarding medication delivery devices and/or systems, such as, for example, integrated systems, is provided in U.S. Patent Application Publication No. US2006/0224141, published on Oct. 5, 2006, entitled "Method and System for Providing Integrated Medication Infusion and Analyte Monitoring System", and U.S. Patent Application Publication No. US2004/0254434, published on Dec. 16, 2004, entitled "Glucose Measuring Module and Insulin Pump Combination," the disclosure of each of which is incorporated by reference herein in its entirety. Medication delivery devices which may be provided with analyte measurement system as described herein include, e.g., a needle, syringe, pump, catheter, inhaler, transdermal patch, or combination thereof. In some embodiments, the medication delivery device or system may be in the form of a drug delivery injection pen such as a pen-type injection device incorporated within the housing of an analyte measurement system. Additional information is provided in U.S. Pat. Nos. 5,536,249 and 5,925,021, the disclosures of each of which are incorporated by reference herein in their entirety.

Communication Interface

As discussed previously herein, an analyte measurement system according to the present disclosure can be configured to include a communication interface. In some embodiments, the communication interface includes a receiver and/or transmitter for communicating with a network and/or another device, e.g., a medication delivery device and/or a patient monitoring device, e.g., a continuous glucose monitoring device. In some embodiments, the communication interface is configured for communication with a health management system, such as the CoPilot™ system available from Abbott Diabetes Care Inc., Alameda, Calif.

The communication interface can be configured for wired or wireless communication, including, but not limited to, radio frequency (RF) communication (e.g., Radio-Frequency Identification (RFID), Zigbee communication protocols, WiFi, infrared, wireless Universal Serial Bus (USB), Ultra Wide Band (UWB), Bluetooth® communication protocols, and cellular communication, such as code division multiple access (CDMA) or Global System for Mobile communications (GSM).

In one embodiment, the communication interface is configured to include one or more communication ports, e.g., physical ports or interfaces such as a USB port, an RS-232 port, or any other suitable electrical connection port to allow data communication between the analyte measurement system and other external devices such as a computer terminal (for example, at a physician's office or in hospital environment), an external medical device, such as an infusion device or including an insulin delivery device, or other devices that are configured for similar complementary data communication.

In one embodiment, the communication interface is configured for infrared communication, Bluetooth® communication, or any other suitable wireless communication protocol to enable the analyte measurement system to communicate with other devices such as infusion devices, analyte monitoring devices, computer terminals and/or networks, communication enabled mobile telephones, personal digital assistants, or any other communication devices which the patient or user of the analyte measurement system may use in conjunction therewith, in managing the treatment of a health condition, such as diabetes.

In one embodiment, the communication interface is configured to provide a connection for data transfer utilizing Internet Protocol (IP) through a cell phone network, Short Message Service (SMS), wireless connection to a personal computer (PC) on a Local Area Network (LAN) which is connected to the internet, or WiFi connection to the internet at a WiFi hotspot.

In one embodiment, the analyte measurement system is configured to wirelessly communicate with a server device via the communication interface, e.g., using a common standard such as 802.11 or Bluetooth® RF protocol, or an IrDA infrared protocol. The server device could be another portable device, such as a smart phone, Personal Digital Assistant (PDA) or notebook computer; or a larger device such as a desktop computer, appliance, etc. In some embodiments, the server device has a display, such as a liquid crystal display (LCD), as well as an input device, such as buttons, a keyboard, mouse or touch-screen. With such an arrangement, the user can control the analyte measurement system indirectly by interacting with the user interface(s) of the server device, which in turn interacts with the analyte measurement system across a wireless link.

In some embodiments, the communication interface is configured to automatically or semi-automatically communicate data stored in the analyte measurement system, e.g., in an optional data storage unit, with a network or server device using one or more of the communication protocols and/or mechanisms described above.

Input Unit

As discussed previously herein, an analyte measurement system according to the present disclosure can be configured to include an input unit and/or input buttons coupled to the housing of the analyte measurement system and in communication with a controller unit and/or processor. In some embodiments, the input unit includes one or more input buttons and/or keys, wherein each input button and/or key is designated for a specific task. Alternatively, or in addition, the input unit may include one or more input buttons and/or keys that can be 'soft buttons' or 'soft keys'. In the case where one or more of the input buttons and/or keys are 'soft buttons' or 'soft keys', these buttons and/or keys may be used for a variety of functions. The variety of functions may be determined based on the current mode of the analyte measurement system, and may be distinguishable to a user by the use of button instructions shown on an optional display unit of the analyte measurement system. Yet another input method may be a touch-sensitive display unit, as described in greater detail below.

In addition, in some embodiments, the input unit is configured such that a user can operate the input unit to adjust time and/or date information, as well as other features or settings associated with the operation of an analyte measurement system.

Display Unit

As discussed previously herein, in some embodiments, an analyte measurement system according to the present disclosure includes an optional display unit or a port for coupling an optional display unit to the analyte measurement system. The display unit is in communication with a control unit and/or processor and displays the analyte test strip signals and/or results determined from the analyte test strip signals including, for example, analyte concentration, rate of change of analyte concentration, and/or the exceeding of a threshold analyte concentration (indicating, for example, hypo- or hyperglycemia).

The display unit can be a dot-matrix display, e.g., a dot-matrix LCD display. In some embodiments, the display unit includes a liquid-crystal display (LCD), thin film transistor liquid crystal display (TFT-LCD), plasma display, light-emitting diode (LED) display, seven-segment display, E-ink (electronic paper) display or combination of two or more of the above. The display unit can be configured to provide, an alphanumeric display, a graphical display, a video display, an audio display, a vibratory output, or combinations thereof. The display can be a color display. In some embodiments, the display is a backlit display.

The display unit can also be configured to provide, for example, information related to a patient's current analyte concentration as well as predictive analyte concentrations, such as trending information.

In some embodiments an input unit and a display unit are integrated into a single unit, for example, the display unit can be configured as a touch sensitive display, e.g., a touch-screen display, where the user may enter information or commands via the display area using, for example, the user's finger, a stylus or any other suitable implement, and where, the touch sensitive display is configured as the user interface in an icon driven environment, for example.

In some embodiments, the display unit does not include a screen designed to display results visually. Instead, in some embodiments the optional display unit is configured to communicate results audibly to a user of the analyte measurement system, e.g., via an integrated speaker, or via separate speakers through a headphone jack or Bluetooth® headset.

Expanding Menu Item for Improved Readability

In some embodiments, the display unit includes a graphical user interface including a plurality of menu items, wherein the display unit is configured to provide clarification with respect to the meaning of a menu item based on a user's response speed with respect to a user input for the menu item. The menu item could take any of a variety of forms, e.g., text, icon, object or combination thereof.

In one embodiment, the graphical user interface includes a menu which in turn includes a plurality of selectable menu items. As a user navigates through the menu, e.g., by highlighting or scrolling through individual menu items, a menu item that is either unreadable or incomprehensible to the user could cause the user to pause over a menu item to be selected. In one embodiment, a choice can be presented to the user, e.g., using a dedicated physical button on an input unit, or a soft key on the menu, that offers further explanation of the item to be selected without actually selecting the item. For example, the graphical user interface can be configured such that after a pre-determined period of time a soft key offers an explanation of the menu item to be selected, e.g., by displaying a soft key with the word "MORE", "ADDITIONAL INFORMATION", "EXPAND", "MAGNIFY", "HELP" or a variation thereof displayed thereon.

The pre-determined period of time may be based on a fixed factory preset value, a value set by the user or a health care provider, or through an adaptive mechanism based on an analysis of the user's speed of navigation from past interactions with the graphical user interface. In one embodiment, the pre-determined period of time is from about 5 to about 20 seconds, e.g., from about 10 to about 15 seconds.

If the offer for clarification and/or additional information is selected, e.g., by pressing the softkey, then the menu item to be selected can be displayed in a "high emphasis" mode, e.g., where the item is displayed as if a magnifying lens is held on top of the selected item. In some embodiments, additional emphasis of the menu item to be selected can be provided, e.g., by making the menu item change color, blink, or increase in size to a pre-determined maximum limit.

Support for Intermittent Analyte Determination using an Analyte Sensor

In some embodiments, an analyte measurement system according to the present disclosure is further configured to receive analyte concentration data and/or signals indicative of an analyte concentration from an analyte sensor, e.g., an implanted or partially implanted analyte sensor or a radio-frequency (RF)-powered measurement circuit coupled to an implanted or partially implanted analyte sensor. In some embodiments, the analyte sensor is a self-powered analyte sensor. An analyte measurement system according to the present disclosure may include software configured to analyze signals received from the analyte sensor. Additional information related to self-powered analyte sensors and methods of communicating therewith are provided in U.S. Patent Application Publication No. 2010/0213057, the disclosure of which is incorporated by reference herein in its entirety.

Integrated Bar Code

In an embodiment, an analyte measurement system according to the present disclosure is integrated with a bar-coding system. The barcoding system may be laser or LED based, and may be used for identification of analyte test strips, patient, health care professional, etc. For example, the analyte measurement system may include a barcode reader disposed in the housing. The housing would further require a internal circuitry and a barcode scan engine for processing of a scan. Additional examples of such a bar coding system is provided in U.S. Pat. No. 7,077,328, which has been incorporated herein by reference in its entirety.

Anti-Microbial Thin Film Cover

In an embodiment, an analyte measurement system according to the present disclosure is provided with an anti-microbial thin film cover. A common problem with many analyte measurement systems is that the housing cracks, degrades, and generally wears down due to the harsh chemicals that are used to disinfect the analyte measurement system in hospital and clinical environments. By placing an anti-microbial plastic film over the analyte measurement system, the life-cycle of the system can be prolonged because the plastic film is subjected to the disinfectants, rather than the system housing itself. When the plastic film begins to degrade, it can be removed and replaced. The plastic film also adds an additional layer of sterility to the system. The plastic film may be transparent, and applied over the display and/or user interface. One side of the plastic film would contain anti-microbial chemistry, while the back side of the plastic film would contain a thin layer of adhesive.

Analytes

A variety of analytes can be detected and quantified using the disclosed analyte measurement system. Analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006 and U.S. Pat. No. 6,638,716, the disclosures of each of which are incorporated by reference herein in their entirety.

CONCLUSION

The foregoing description of the invention has been presented for purposes of illustration and description. It is not intended to be exhaustive or to limit the invention to the precise form disclosed. Other modifications and variations may be possible in light of the above teachings. The embodiments were chosen and described in order to best explain the principles of the invention and its practical application, and to thereby enable others skilled in the art to best utilize the invention in various embodiments and various modifications as are suited to the particular use contemplated. It is intended that the appended claims be construed to include other alternative embodiments of the invention; including equivalent structures, components, methods, and means.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described above to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The publications discussed herein are provided solely for their disclosure prior to the filing date of the application. Nothing herein is to be construed as an admission that the embodiments of the invention are not entitled to antedate such publication by virtue of prior invention. Further, the dates of publication provided may be different from the actual publication dates which may need to be independently confirmed.

It is to be appreciated that the Detailed Description section, and not the Summary and Abstract sections, is intended to be used to interpret the claims. The Summary and Abstract sections may set forth one or more, but not all exemplary embodiments of the present invention as contemplated by the inventor(s), and thus, are not intended to limit the present invention and the appended claims in any way.

What is claimed is:

1. A method of using an analyte measurement system, the method comprising:
   removing a first replaceable strip port module from a strip port cavity of a housing of an analyte meter, wherein the analyte meter comprises the housing and electrical connections disposed with the strip port cavity within the housing, wherein the analyte meter lacks an integrated analyte test strip port in the meter housing, the first replaceable strip port module comprises:
   a module housing comprising an interface aperture,
   an analyte test strip port, and
   an electrical interface comprising a plurality of electrical contacts coupled to the analyte test strip port within the module housing and extending from the test strip port to the interface aperture; and
   positioning a second replaceable strip port module in the analyte meter housing, wherein the second replaceable strip port module comprises:
   an output interface positioned wholly within the meter housing of the analyte meter and in electrical communication with the input interface of the analyte meter,
   an analyte test strip port disposed external to the meter housing of the analyte meter, and
   a connector linking the output interface at a distal end and the analyte test strip port at a proximal end.

2. The method of claim 1, wherein the analyte test strip is a glucose test strip.

3. The method of claim 1, wherein the analyte test strip is a ketone test strip.

4. The method of claim 1, wherein the connector is a retractable cord.

5. The method of claim 1, wherein the analyte meter comprises a health management communication interface.

6. The method of claim 5, wherein the health management communication interface is a wired interface.

7. The method of claim 5, wherein the health management communication interface is a wireless interface.

8. The method of claim 7 wherein the health management communication interface is a wireless interface configured for communication via radio frequency communication, Zigbee communication protocols, WiFi, infrared, wireless Universal Serial Bus, Ultra Wide Band, Bluetooth® communication protocols, or cellular communication protocols.

9. The method of claim 1, wherein the system comprises a docking station for the analyte meter.

10. The method of claim 9, wherein the docking station comprises a transmitter that transmits data over a data network.

11. The method of claim 9, wherein the docking station comprises a battery charger.

12. The method of claim 1, wherein the analyte meter comprises a user interface.

13. The method of claim 12, wherein the user interface is a touchscreen monitor.

14. The method of claim 1, wherein the analyte test strip port comprises a test strip ejector.

15. The method of claim 1, wherein the analyte test strip port comprises a sealing member.

16. The method of claim 1, wherein the analyte test strip port comprises an internal beveled face.

* * * * *